United States Patent
Larse

(10) Patent No.: US 11,419,301 B2
(45) Date of Patent: *Aug. 23, 2022

(54) STRAWBERRY PLANT NAMED 'YAKIMA'

(71) Applicant: Sweet Darling Sales, Inc., Aptos, CA (US)

(72) Inventor: John Larse, Watsonville, CA (US)

(73) Assignee: Sweet Darling Sales, Inc., Aptos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/092,075

(22) Filed: Nov. 6, 2020

(65) Prior Publication Data
US 2021/0051909 A1    Feb. 25, 2021

Related U.S. Application Data

(63) Continuation of application No. 16/873,069, filed on Jan. 28, 2020, now Pat. No. Plant 32,800.

(60) Provisional application No. 62/797,491, filed on Jan. 28, 2019.

(51) Int. Cl.
*A01H 6/74* (2018.01)
*A01H 5/08* (2018.01)

(52) U.S. Cl.
CPC ............. *A01H 6/7409* (2018.05); *A01H 5/08* (2013.01)

(58) Field of Classification Search
CPC .................................................. A01H 6/7409
USPC .......................................................... Plt./208
See application file for complete search history.

(56) References Cited

U.S. PATENT DOCUMENTS

| | | |
|---|---|---|
| PP19,767 P2 | 2/2009 | Shaw et al. |
| PP25,849 P3 | 9/2015 | Larse |
| PP30,326 P2 * | 4/2019 | Bagdasarian ........ A01H 6/7409 Plt./209 |
| PP32,800 P3 * | 2/2021 | Larse ................... A01H 6/7409 Plt./208 |
| 2020/0245516 P1 | 7/2020 | Larse |

* cited by examiner

*Primary Examiner* — David H Kruse
(74) *Attorney, Agent, or Firm* — Cooley LLP

(57) ABSTRACT

The present invention provides a new and distinct strawberry variety designated as 'Yakima' (a.k.a. '109733'). A strawberry variety designated 'Yakima' is disclosed. The disclosure relates to asexual propagules of strawberry variety designated 'Yakima', to the plants and plant parts of strawberry variety designated 'Yakima', and to methods for producing an asexually reproduced strawberry plant 'Yakima.'

19 Claims, 5 Drawing Sheets
(5 of 5 Drawing Sheet(s) Filed in Color)

STRAWBERRY PLANT NAMED 'YAKIMA'

CROSS-REFERENCE TO RELATED APPLICATION

This application is a continuation of U.S. patent application Ser. No. 16/873,069, filed on Jan. 28, 2020, now U.S. Plant Patent No. PP32,800, issued on Feb. 9, 2021, which claims the benefit of priority to U.S. Provisional Patent Application No. 62/797,491, filed on Jan. 28, 2019, each of which is herein incorporated by reference in its entirety for all purposes.

BACKGROUND OF THE INVENTION

The present invention relates to a new and distinct short-day strawberry variety designated as 'Yakima' (a.k.a. '109733').

'Yakima' (a.k.a. '109733') is the result of a controlled-cross between a female parent cultivar designated (Aida', a.k.a. '106734',) an unpatented, proprietary strawberry plant variety made by the inventor and a male parent cultivar designated 'Lili' (a.k.a. '101983', U.S. Plant Patent No. PP25,849) and was first fruited in Watsonville, Calif. growing fields. Following selection and during testing, the plant was originally designated '109733' and subsequently named 'Yakima'.

The new variety was asexually reproduced via runners (stolons) by the inventor at Watsonville, Calif. Asexual propagules from the original source have been tested in Watsonville growing fields and to a limited extent, grower fields in high elevation. The properties of this variety were found to be transmissible by such asexual reproduction. This cultivar is stable and reproduces true to type in successive generations of asexual reproduction.

DESCRIPTION OF THE DRAWINGS

The patent or application file contains at least one drawing executed in color. Copies of this patent or patent application publication with color drawing(s) will be provided by the Office upon request and payment of the necessary fee.

The accompanying color photographs depict various characteristics of the cultivar as nearly true as possible to make color reproductions.

SUMMARY OF THE INVENTION

Figure 1:
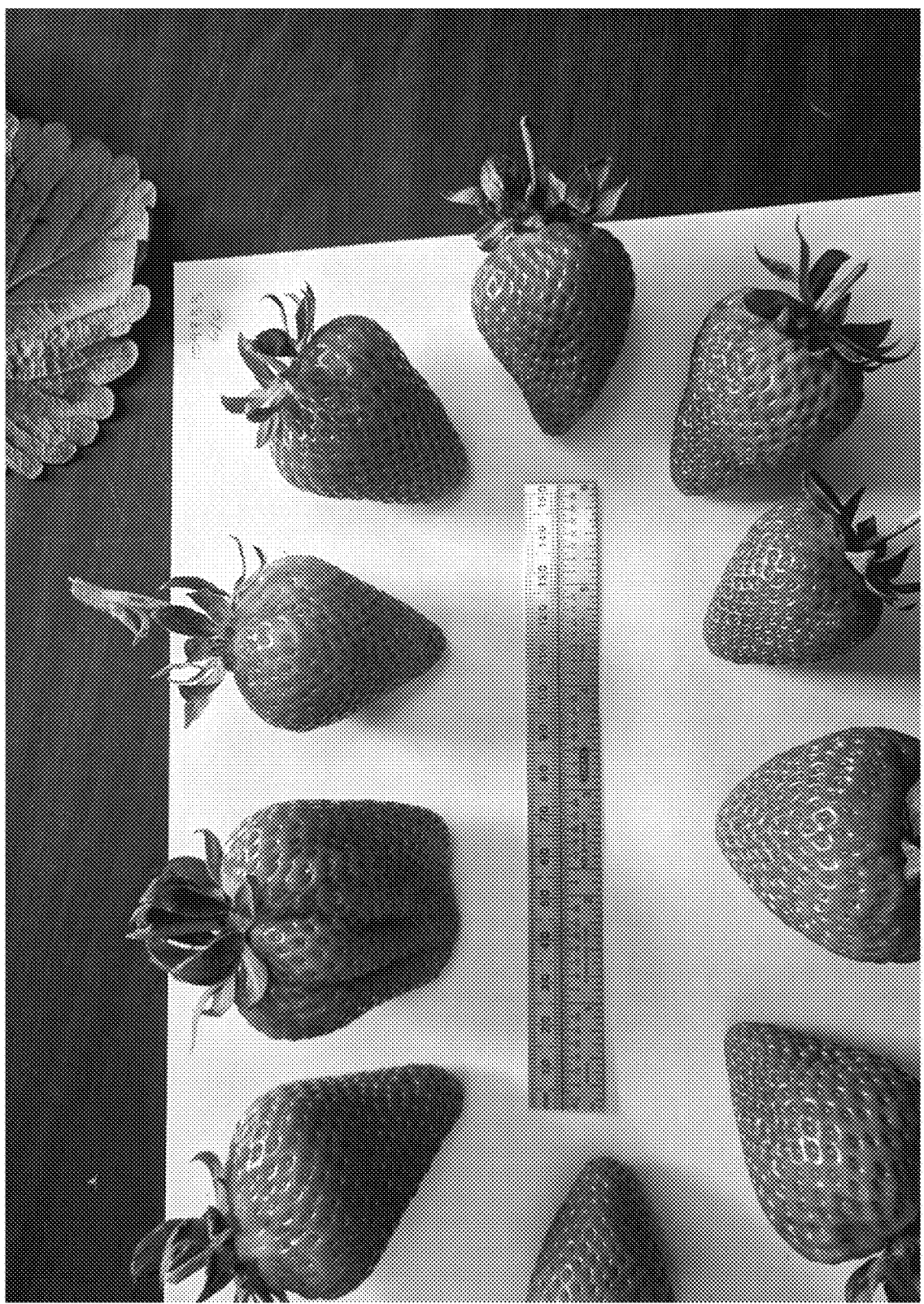
FIG. 1 shows 'Yakima' fruit.
Figure 2:
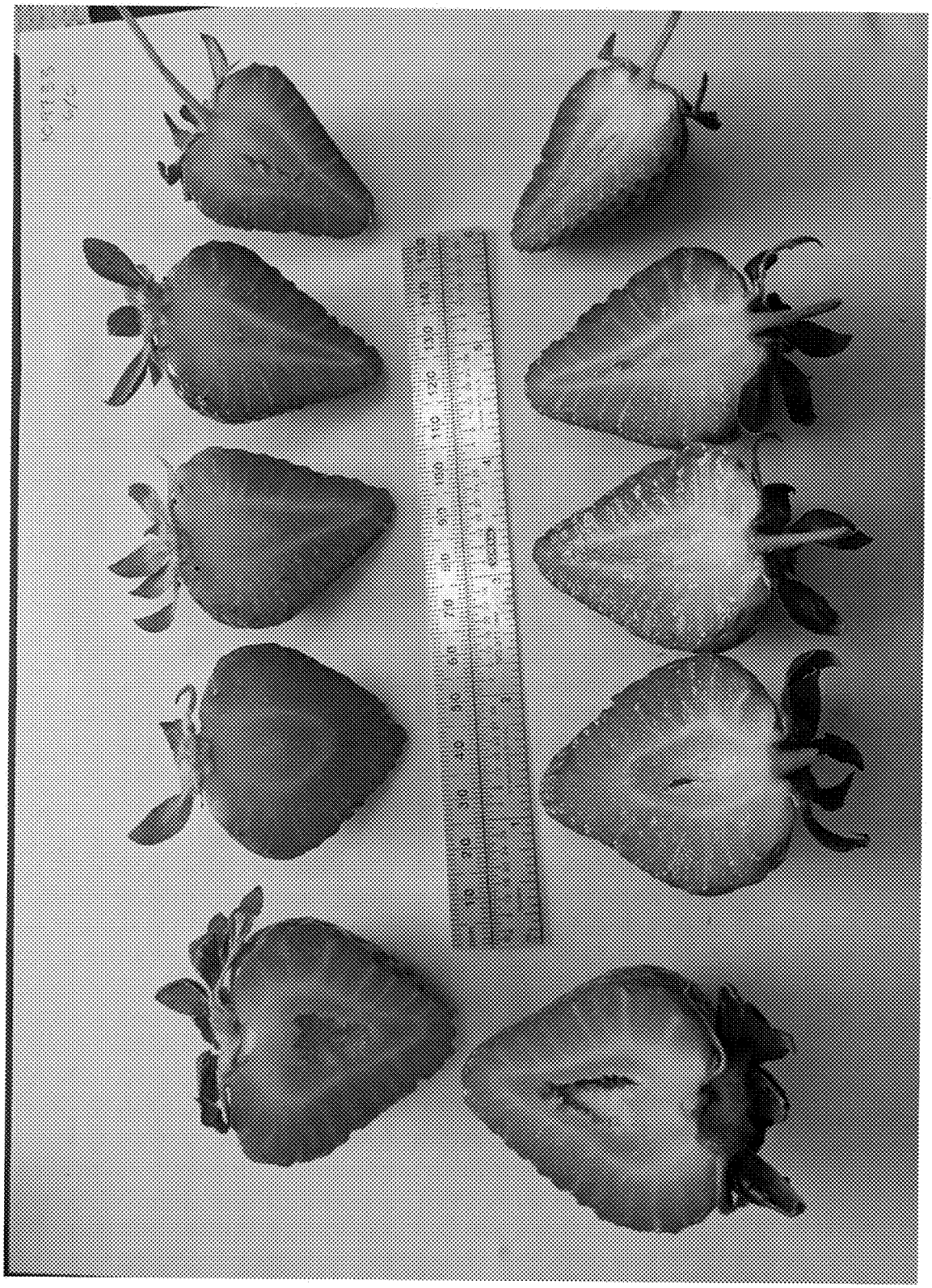
FIG. 2 shows 'Yakima' fruit.
Figure 3A:
FIG. 3A and FIG. 3B show 'Yakima' strawberry plants with fruit.
Figure 3B:
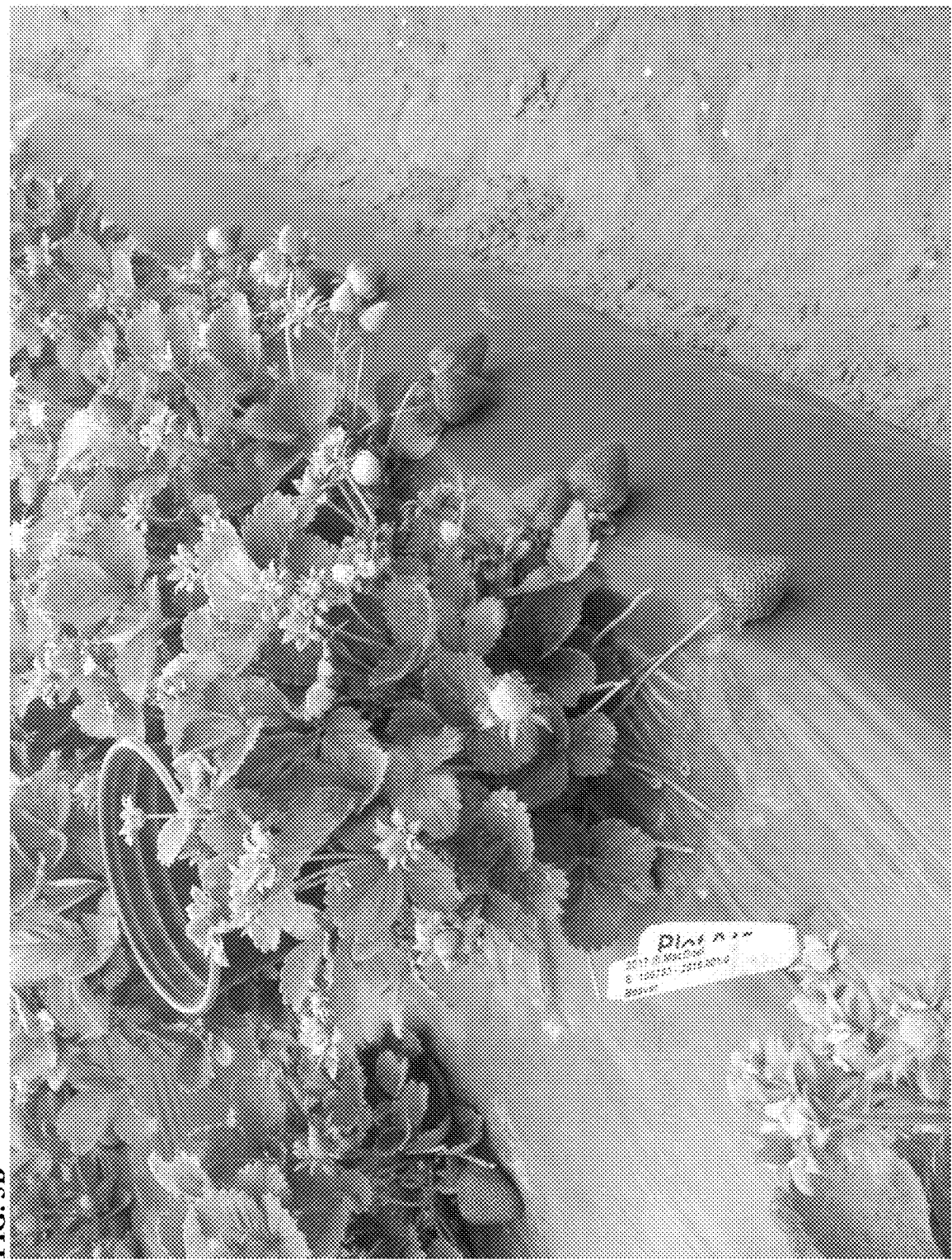
Figure 4:
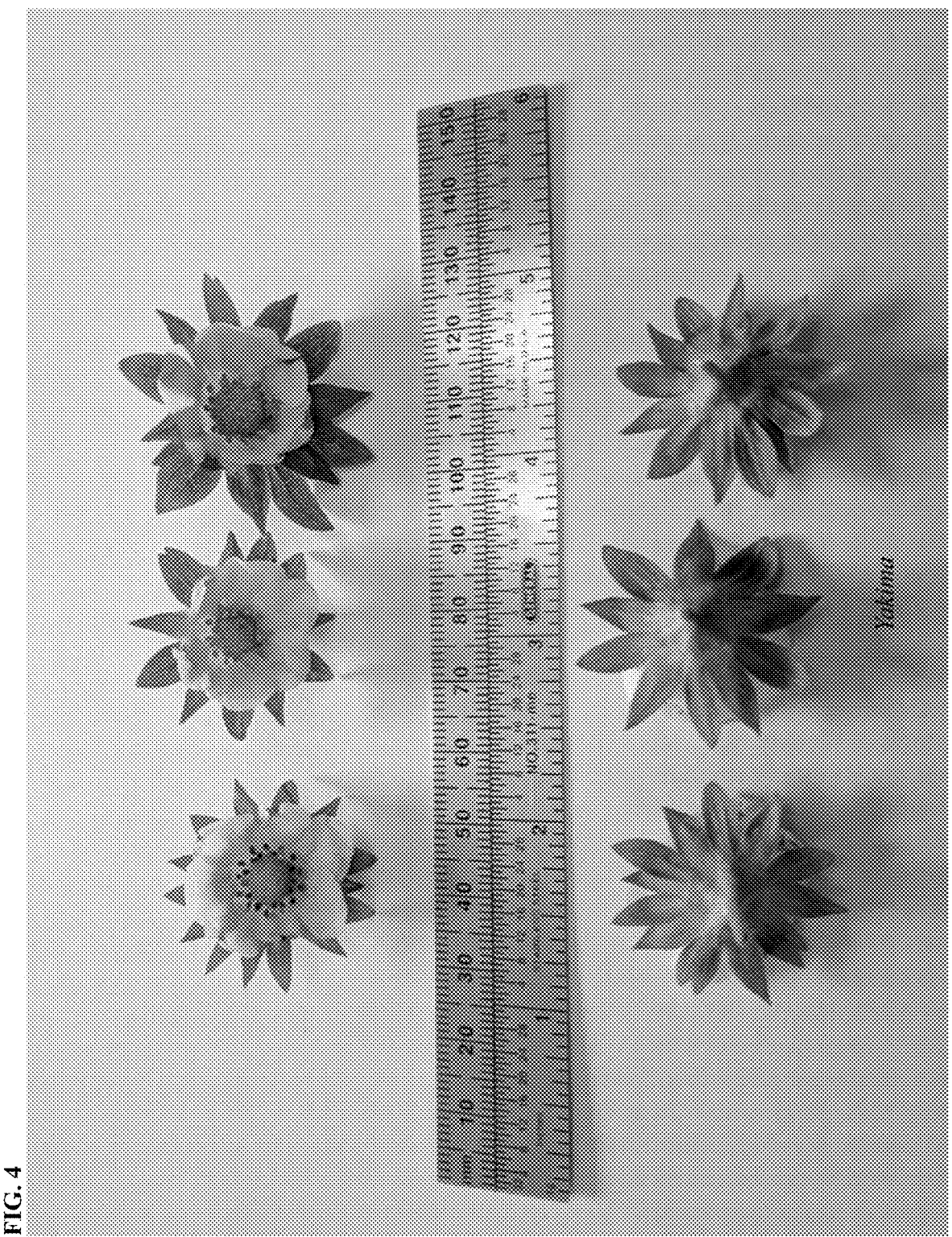
FIG. 4 shows flowers of 'Yakima' strawberry plant variety.

This invention relates to a new and distinctive strawberry cultivar designated as 'Yakima'. This cultivar is primarily adapted to the climate and growing conditions of the central coast of California. This region provides the necessary temperatures required for it to produce a strong vigorous plant and to remain in fruit production from March through October. The nearby Pacific Ocean provides the needed humidity and moderate day temperatures and evening chilling to maintain fruit quality for the production months. 'Yakima' (a.k.a. '109733')

The following traits and photographs in combination distinguish the strawberry variety 'Yakima' from known strawberry varieties. In addition, the new cultivar was confirmed to be a unique strawberry germplasm when tested against the California Seed & Plant Lab, Inc. (Elverta, Calif.) database using Short Sequence Repeats (SSRs). Plants for the botanical measurements in the present application were grown as annuals. Any color references are made to The Royal Horticultural Society Colour Chart, 1995 Edition, except where general terms of ordinary dictionary significance are used. The botanical measurements listed in Table 1 were made and recorded during the month of June.

'Yakima' is distinguished from its paternal parent by the percent of marketable fruit (Table 2), for 'Yakima' percent marketable fruit is twenty percentile points greater than its paternal parent 'Lili' (U.S. Plant Patent No. PP25,849). 'Yakima' is distinguished from its maternal parent 'Aida' by the figure of its fruit. The fruit of 'Yakima' is mostly conical, different from the longer somewhat flat wedge shape of the fruit of its parent 'Aida'. 'Yakima' is similar to the strawberry plant named 'Monterey' (U.S. Plant Patent No. PP19,767), but possesses several distinguishing traits from Monterey. 'Yakima' is distinguished from 'Montery' by the thicker canopy of 'Yakima' and dark green foliage color of 'Yakima'.

TABLE 1

| Characteristic Type | Characteristic | Yakima |
| --- | --- | --- |
| General | Plant Habit | annual |
| | Plant Growth Habit | upright |
| | Day length | neutral |
| | Planting season | Fall |
| | Height | 35 cm |
| | Width | 36 cm |
| | Density of foliage | medium |
| | Plant vigor | high |
| | Freezing Quality | moderate |
| | Rain/weather tolerance | moderate to high |
| | Harvest Ease | moderate |
| Leaf | Leaf Shape | concave |
| | Terminal leaflet width | 90 mm |
| | Terminal leaflet length | 100 mm |
| | Terminal leaflet length/width ratio | 1.11 |
| | Teeth per terminal leaflet | 17 to 19 |
| | Shape of the terminal leaflet base | rounded |
| | Shape of terminal leaflet in cross-section | concave to straight |
| | Shape of the terminal leaflet margin | serrate to crenate |
| | Color of upper side of leaflet | RHS 136A |
| | Color of lower side of leaflet | RHS 139C |
| | Leaf blistering | weak |
| | Leaf glossiness | medium |
| | Leaf variegation | absent |
| | Number of leaflets | 150 to 219 |
| | Terminal Leaflet margin | revolute |
| | Terminal Leaflet shape | Orbicular |
| | Terminal Leaflet shape of apex | Rounded |

TABLE 1-continued

| Characteristic Type | Characteristic | Yakima |
|---|---|---|
| Limbs | Petiole length | 25.5 cm |
| | Petiole diameter | 3.18 to 4.26 mm |
| | Petiole pubescence | medium |
| | Petiole pose of hairs | horizontal |
| | Petiole color | RHS 145A |
| | Petiolule length | 1.0 to 1.5 cm |
| | Petiolule diameter | 2.08 to 2.70 mm |
| | Stipule length | 3.5 cm |
| | Stipule width | 0.9 to 1.0 cm |
| | Stipule pubescence | dense |
| | Stipule anthocyanin | absent |
| | Stipule color (color code) | RHS 145C |
| | Pedicel color (color code) | RHS 145A |
| | Attitude of hairs on peduncle and pedicel | |
| | Peduncle size | medium |
| Inflorescence | Inflorescence position relative to foliage | above |
| | Flower arrangement of petals | touching |
| | Flower size | medium |
| | Flower diameter | 2.28 cm |
| | Petal shape | orbicular |
| | Petal apex | rounded |
| | Petal margin | entire |
| | Petal base shape | concave |
| | Petal length | 1.17 cm |
| | Petal width | 1.15 cm |
| | Petal length/width ratio | 1.02 |
| | Petal number per flower | 5 to 7 |
| | Number of flowers | 16 to 36 |
| | Upper Petal color | RHS 155D |
| | Lower Petal color | RHS 155D |
| | Floral Calyx Diameter | 4.08 cm |
| | Corolla diameter | 2.28 cm |
| | Calyx diameter relative to corolla | larger |
| | Inner calyx | same |
| | Sepal shape | elliptical |
| | Sepal apex | convex |
| | Sepal margin | entire |
| | Sepal length | 1.93 cm |
| | Sepal width | 0.61 cm |
| | Sepal number per flower | 12 |
| | Receptacle color | RHS 4A |
| | Fertility | not tested |
| | Time of flowering (50% of plants in bloom) | May |
| | Shape of stigma | rounded |
| | Color of stigma | RHS 4A |
| | Length of style | 5 mm |
| | Color of style | RHS 4A |
| | Color of the ovary | RHS 138D |
| | Number of stamen | 25 |
| | Length of the stamens | 2.3 mm |
| | Shape of anther | dorsifixed |
| | Size of anther | 1.39 mm |
| | Color of anther | RHS 6A |
| | Amount of pollen | scarce to moderate |
| | Color of pollen | RHS 163B |
| | Color of filament | RHS 145C |
| | Length of filament | 1.2 to 2.8 mm |
| Fruit | Fruiting truss length | 6 to 17 cm |
| | Fruiting truss diameter | 1.4 mm |
| | Number of fruit per truss | 1 to 5 |
| | Fruit length | 5.3 cm |
| | Fruit width | 4.3 cm |
| | Fruit skin color | RHS 45A |
| | Fruit flesh color excluding core | RHS 44A |
| | Fruit core color | RHS 41B |
| | Fruit length/width ratio | 1.23 |
| | Fruit weight | 33 g |
| | Relative fruit size | medium to large |
| | Predominant fruit shape | long conic and long wedge |
| | Shape difference between primary & secondary fruits | No shape difference |
| | Width of band without of achenes | narrow |
| | Fruit glossiness | strong |
| | Position of achenes | below surface |
| | Achene color | RHS 151D |
| | Achenes per fruit | 340 |
| | Achene weight | 0.238 g |
| | Position of calyx | even |
| | Fruit Calyx Diameter | 5.5 cm |
| | level of adherence of calyx | medium |
| | Color of calyx | RHS 137C |
| | Pose of calyx segments | reflexed |
| | Size of calyx in relation to fruit | same |
| | Firmness of flesh | medium to firm |
| | Evenness of flesh color | nearly even |
| | Fruit hollow length | 2.3 cm |
| | Fruit hollow width | 1.4 cm |
| | Fruit hollow length/width ratio | 1.64 |
| | Hollow center | absent to medium |
| | Sweetness | 7 to 14 Brix |
| | pH | 3.33 |
| | Texture when tasted | fine to medium |
| | Time of flowering | April |
| | Time of fruit ripening | May |
| | Harvest maturity (50% of plants with ripe fruit) | June |
| | Type of bearing | day netural |
| | Grams of fruit per plant | June: 721 g |
| | Yield (lb per acre) | June: 31,791 lb/acre |
| | Firmness | soft to firm |
| | Surface Texture | smooth |
| | Appearance Score | 4 |
| | Storage longevity | 5 to 10 days |
| | Cull rate: 1-% Usable | <10% |
| Stolon | Stolon number | 1 to 3 |

TABLE 2

Strawberry fruit summary statistic means of yield, percent marketable, flavor, firmness, figure and size during weeks 15 to 37 over years; Watsonville, California.
gGrams (goodgrams or marketable fruit)

| strawberry plant variety | μ fheight mm | μ fwidth mm | fht/fw | μ hardness | μ gGrams/ clone | μ kilos/ acre | μ % Usable | μ frtSizeGrms | μ skin-r | μ flavor |
|---|---|---|---|---|---|---|---|---|---|---|
| Yakima | 51.0304 | 40.2999 | 1.26626 | 8.79292 | 1622 | 32,443 | 0.905 | 31.39 | 2.13004 | 2.84304 |
| Lily | 40.2262 | 35.8540 | 1.12194 | 8.78205 | 1304 | 26,089 | 0.797 | 29.95 | 2.09745 | 3.05084 |

DEPOSIT INFORMATION

A deposit of the 'YAKIMA' strawberry plant is maintained by Sweet Darling Sales, Inc., 24 Seascape Village, Aptos, Calif. 95003. In addition, a tissue culture of the 'YAKIMA' plant of this disclosure has been deposited with an International Depositary Authority as established under the Budapest Treaty according to 37 CFR 1.803(a)(1). Applicant has deposited tissues of the 'YAKIMA' plant at the Provasoli-Guillard National Center for Marine Algae and Microbiota (NCMA), located at the Bigelow Laboratory for Ocean Science at 60 Bigelow Drive, East Boothbay, Me. 04544.

The 'YAKIMA' tissues have been deposited and accepted under the Budapest Treaty as NCMA No. 202107021 on Jul. 13, 2021.

To satisfy the enablement requirements of 35 U.S.C. 112, and to certify that the deposit of the isolated strain (i.e., strawberry plant) of the present disclosure meets the criteria set forth in 37 C.F.R. 1.801-1.809 and Manual of Patent Examining Procedure (MPEP) 2402-2411.05, Applicant hereby makes the following statements regarding the deposited 'YAKIMA' strawberry variety (deposited as NCMA No. 202107021):

1. During the pendency of this application, access to the disclosure will be afforded to the Commissioner upon request;
2. All restrictions on availability to the public will be irrevocably removed upon granting of the patent under conditions specified in 37 CFR 1.808;
3. The deposit will be maintained in a public repository for a period of 30 years or 5 years after the last request or for the effective life of the patent, whichever is longer;
4. A test of the viability of the biological material at the time of deposit will be conducted by the public depository under 37 C.F.R. 1.807; and
5. The deposit will be replaced if it should ever become unavailable.

Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of the tissue cultures of the same variety with the NCMA.

What is claimed:

1. Asexual propagules of strawberry plant designated Yakima, wherein a representative sample of the asexual propagules has been deposited under NCMA No. 202107021.

2. The asexual propagules of claim 1, wherein the asexual propagules are stolons.

3. A strawberry plant or plant part thereof, produced by growing the asexual propagules of claim 1, wherein the strawberry plant has all of the physiological and morphological characteristics of strawberry plant designated Yakima deposited under NCMA No. 202107021 when grown under the same environment conditions.

4. The strawberry plant, or plant part of claim 3, wherein the strawberry plant part is selected from the group consisting of a leaf, a flower, a fruit, an achene and a stolon.

5. A strawberry plant, or plant part thereof, produced from the stolons of claim 2, wherein the strawberry plant has all of the physiological and morphological characteristics of strawberry plant designated Yakima deposited under NCMA No. 202107021 when grown under the same environment conditions.

6. A strawberry plant, or plant part thereof, produced from the stolons of claim 4, wherein the strawberry plant has all of the physiological and morphological characteristics of strawberry plant designated Yakima deposited under NCMA No. 202107021 when grown under the same environment conditions.

7. A strawberry plant, or plant part thereof, produced by asexual reproduction of the strawberry plant, or plant part thereof, of claim 3, wherein the asexually reproduced strawberry plant has all of the physiological and morphological characteristics of strawberry plant designated Yakima deposited under NCMA No. 202107021 when grown under the same environment conditions.

8. A strawberry plant, or plant part thereof, having all of the physiological and morphological characteristics of strawberry plant designated Yakima deposited under NCMA No. 202107021 when grown under the same environment conditions.

9. The strawberry plant, or the plant part of claim 8, wherein the plant part is a fruit.

10. The strawberry plant, or the plant part of claim 8, wherein the plant part is a stolon.

11. A method for producing an asexually reproduced strawberry plant, the method comprising asexually reproducing the strawberry plant, or plant part thereof, of claim 3 and growing the resultant asexually reproduced strawberry plant.

12. The method of claim 11, further comprising harvesting a fruit from the asexually reproduced plant.

13. A fruit produced by the method of claim 12, wherein the fruit has all of the physiological and morphological characteristics of strawberry plant designated Yakima deposited under NCMA No. 202107021 when grown under the same environment conditions.

14. A method for producing an asexually reproduced strawberry plant, the method comprising asexually reproducing the strawberry plant, or plant part thereof, of claim 5 and growing the resultant asexually reproduced strawberry plant.

15. The method of claim 14, further comprising harvesting a fruit from the asexually reproduced plant.

16. A fruit produced by the method of claim 15, wherein the fruit has all of the physiological and morphological characteristics of strawberry plant designated Yakima deposited under NCMA No. 202107021 when grown under the same environment conditions.

17. A method for producing an asexually reproduced strawberry plant, the method comprising asexually reproducing the strawberry plant, or plant part thereof, of claim 8 and growing the resultant asexually reproduced strawberry plant.

18. The method of claim 17, further comprising harvesting a fruit from the asexually reproduced plant.

19. A fruit produced by the method of claim 18, wherein the fruit has all of the physiological and morphological characteristics of strawberry plant designated Yakima deposited under NCMA No. 202107021 when grown under the same environment conditions.

* * * * *